United States Patent
Vergunst et al.

(10) Patent No.: US 11,053,210 B2
(45) Date of Patent: Jul. 6, 2021

(54) PROCESS TO CONTINUOUSLY PREPARE A CYCLIC CARBONATE

(71) Applicant: NEW GREEN WORLD B.V., Gouda (NL)

(72) Inventors: Frank Vergunst, Gouda (NL); Sander Laurentius, Gapelle aan den IJssel (NL)

(73) Assignee: NEW GREEN WORLD B.V., Gouda (NL)

( * ) Notice: Subject to any disclaimer, the term of this patent is extended or adjusted under 35 U.S.C. 154(b) by 0 days.

(21) Appl. No.: 16/768,906

(22) PCT Filed: Dec. 18, 2018

(86) PCT No.: PCT/NL2018/050854
§ 371 (c)(1),
(2) Date: Jun. 2, 2020

(87) PCT Pub. No.: WO2019/125151
PCT Pub. Date: Jun. 27, 2019

(65) Prior Publication Data
US 2020/0399239 A1      Dec. 24, 2020

(30) Foreign Application Priority Data

Dec. 22, 2017 (NL) .................................. 2020163

(51) Int. Cl.
*C07D 317/38* (2006.01)
*C07F 5/06* (2006.01)

(52) U.S. Cl.
CPC ............ *C07D 317/38* (2013.01); *C07F 5/069* (2013.01)

(58) Field of Classification Search
CPC .................................................... C07D 317/38
USPC ........................................................ 549/449
See application file for complete search history.

(56) References Cited

FOREIGN PATENT DOCUMENTS

WO      2009109765 A1      9/2009

*Primary Examiner* — Taofiq A Solola
(74) *Attorney, Agent, or Firm* — Nixon Peabody LLP; Ronald I. Eisenstein; Nicole D. Kling

(57) ABSTRACT

Process to continuously prepare a cyclic carbonate product by reacting an epoxide compound with carbon dioxide in the presence of a supported dimeric aluminium salen complex which complex is activated by a halide compound comprising the following steps, (a) contacting carbon dioxide with the epoxide compound in a suspension of liquid cyclic carbonate and the supported dimeric aluminium salen complex which complex is activated by a halide compound, (b) separating part of the cyclic carbonate product from the supported dimeric aluminium salen complex, (c) separating the halide compound from the cyclic carbonate product to obtain purified cyclic carbonate product, (d) use all or part of the halide compound as obtained in step (c) to activate deactivated supported dimeric salen complex.

17 Claims, 2 Drawing Sheets

PROCESS TO CONTINUOUSLY PREPARE A CYCLIC CARBONATE

CROSS-REFERENCE TO RELATED APPLICATIONS

Figure 1:
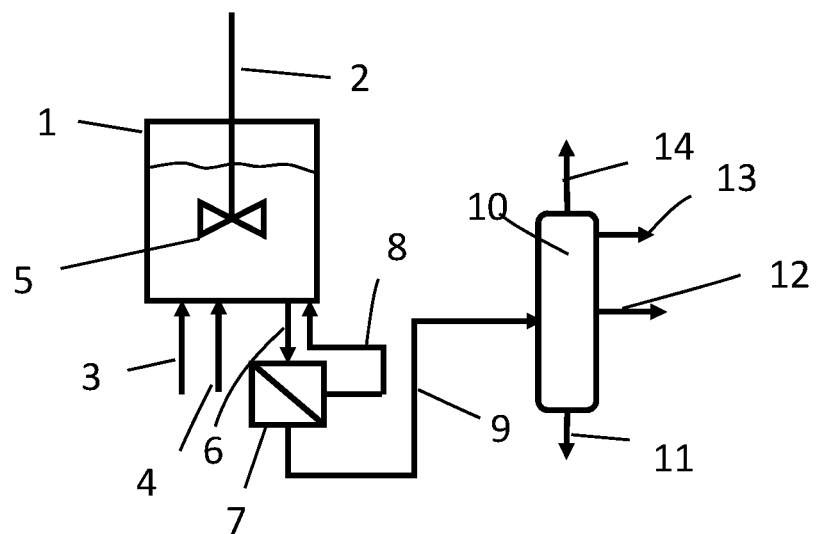

This application is a 35 U.S.C. § 371 National Phase Entry Application of International Application No. PCT/NL2018/050854 filed Dec. 18, 2018, which designates the U.S. and claims benefit under 35 U.S.C. § 119(a) of N.L. Provisional Application No. 2020163 filed Dec. 22, 2017, the contents of which are incorporated herein by reference in their entireties.

The invention is directed to a process to continuously prepare a cyclic carbonate product by reacting an epoxide compound with carbon dioxide in the presence of a supported dimeric aluminium salen complex, which complex is activated by a halide compound.

Such a process is described in EP2257559B1. In this publication a continuous process to prepare ethylene carbonate from ethylene oxide and carbon dioxide is described. The reaction takes place in the presence of a dimeric aluminium salen complex supported on a modified $SiO_2$ support as the catalyst and nitrogen gas. The supported catalyst is present in a tubular reactor and the reactants are supplied to the tubular reactor as a gaseous mixture of ethylene oxide, carbon dioxide and nitrogen. The temperature in the reactor was kept at 60° C. by means of a water bath and the pressure was atmospheric. The yield of ethylene carbonate was 80%.

An advantage of the process of EP2257559B1 is that the reaction conditions may be close to ambient in terms of temperature and atmospheric in terms of pressure. As a result of this the energy consumption of the process is low and less by-products are formed. A disadvantage however of the continuous process described in EP2257559B1 is that the tubular reactor requires external cooling to avoid overheating as a result of the exothermal reaction to ethylene carbonate.

The object of the present invention is to provide a process which can prepare a cyclic carbonate product by reacting an epoxide compound with carbon dioxide at a large scale.

This object is achieved by the following process. Process to continuously prepare a cyclic carbonate product by reacting an epoxide compound with carbon dioxide in the presence of a supported dimeric aluminium salen complex which complex is activated by a halide compound comprising the following steps, (a) contacting carbon dioxide with the epoxide compound in a suspension of liquid cyclic carbonate and the supported dimeric aluminium salen complex which complex is activated by a halide compound, wherein the epoxide compound reacts with the carbon dioxide to the cyclic carbonate product and part of the supported dimeric salen complex deactivates, (b) separating part of the cyclic carbonate product from the supported dimeric aluminium salen complex, to obtain a mixture comprising of the cyclic carbonate product, carbon dioxide, epoxide compound and halide compound, (c) separating the halide compound from the cyclic carbonate product to obtain purified cyclic carbonate product, and (d) use all or part of the halide compound as obtained in step (c) to activate deactivated supported dimeric salen complex.

Applicants found that by performing the reaction in a suspension of the liquid cyclic carbonate product and the supported catalyst complex an efficient process is obtained which does not have the disadvantages of the continuous process described in EP2257559B1. The liquid cyclic carbonate product is an efficient heat transfer medium which avoids local hot spots and possible thermal deactivation of the catalyst complex. No additional nitrogen gas is required. High yields to the desired cyclic carbonate product may be achieved by recycling the non-reacted epoxide to the reactor in step (a). The selectivity of the reaction may be high resulting in that the yield to cyclic carbonate may even be up to 95%. Furthermore by re-using the halide compound to reactivate the supported dimeric aluminium salen complex a low chemical consumption is achieved. Further advantages will be described when describing the preferred embodiments of the invention below.

In step (a) the carbon dioxide is contacted with the epoxide compound in a suspension of liquid cyclic carbonate. The temperature and pressure conditions are chosen such that the cyclic carbonate is in its liquid state. The temperature and pressure conditions are further chosen such that carbon dioxide and epoxide easily dissolve in the liquid cyclic carbonate reaction medium. The temperature may be between 0 and 200° C. and the pressure is between 0 and 5.0 MPa (absolute) and wherein temperature is below the boiling temperature of the cyclic carbonate product at the chosen pressure. At the high end of these temperature and pressure ranges complex reactor vessels will be required. Because favourable results with respect to selectivity and yield to the desired carbonate product are achievable at lower temperatures and pressures it is preferred to perform step (a) at a temperature between 20 and 150° C., more preferably between 40 and 120° C. The absolute pressure is preferably between 0.1 and 1.0 MPa, more preferably between 0.1 and 0.5 MPa and even more preferably between 0.1 and 0.2 MPa.

The content of the supported and halide activated dimeric aluminium salen complex in step (a) may be between 1 wt % and 50 wt % in the liquid cyclic carbonate reaction mixture.

The reactor in which step (a) may be any reactor in which the reactants and catalyst in the liquid reaction mixture can intimately contact and wherein the feedstock can be easily supplied to. Suitably the reactor is a continuously operated reactor comprising the cyclic carbonate product and the suspended supported dimeric aluminium salen complex. To such a reactor carbon dioxide and epoxide may be supplied to and from which continuously cyclic carbonate is withdrawn from. The gaseous carbon dioxide and the gaseous or liquid epoxide may be supplied to a vessel acting as the reactor. The speed at which the gaseous carbon dioxide and the gaseous or liquid epoxide is supplied could agitate the liquid contents of the reactor such that a substantially evenly distributed reaction mixtures results. Sparger nozzle may be used to add a gaseous compound to the reactor. Such agitation may also be achieved by using for example ejectors or mechanical stirring means, like for example impellers. Such reactors may be of the so-called bubble column slurry type reactor and stirred tank reactor. In a preferred embodiment step (a) is performed in a continuously operated stirred reactor wherein carbon dioxide and epoxide compound are continuously supplied to the reactor and wherein part of the cyclic carbonate product is continuously withdrawn as part of a liquid stream. The stirred reactor may be mechanically stirred or stirred by any other means to agitate the mixture as for example described above. More than one reactor may be used in parallel and/or in series with the chosen reactor. Such additional reactors may be the same or different. For example more than one continuously stirred reactors may be operated in series wherein to the first reactor or reactors more reactants are added and/or added in different ratios than to the last reactor. The last reactor may be different in that means are integrated which enable the separation of step (b). Instead of multiple reactors in series a tubular reactor may also be used through which the suspension flows.

In step (b) part of the cyclic carbonate product is separated from the supported dimeric aluminium salen complex to obtain the cyclic carbonate product. Together with part of the cyclic carbonate also part of the unreacted carbon dioxide, unreacted epoxide compound and halide compound are separated from the catalyst complex in step (b). The halide compound is present in the reaction mixture of step (a) and activates the supported dimeric aluminium salen complex. Preferably the halide compound will form a stable complex with the supported dimeric aluminium salen complex. It is found that in time some halide compound will dissolve in the reaction mixture and as a result end up in the cyclic carbonate stream obtained in step (b). The loss of halide compound from step (a) results in that part of the dimeric aluminium salen complex is less activated.

The separation in step (b) may make use of the different mass density and/or size between the cyclic carbonate and the supported dimeric aluminium salen complex. For example separation may be performed making use of centrifugal forces, like for example in a hydrocyclone. Separation making use of the difference in size may be achieved by filtration. Preferably step (b) is performed by filtration and more preferably by means of cross filtration. In such a filtration a flow of the reaction mixture of step (a) flows along the surface of a filter while the cyclic carbonate passes the filter and the supported dimeric aluminium salen complex stays behind. Such a cross flow filter is advantageous because no or almost no cake formation takes place on the surface of the filter as would be the case in dead end filtration. Such a filter may be positioned in the reactor of step (a). The flow along the surface may be achieved by stirring means of the reactor. The optimal filter will depend on the size of the supported dimeric aluminium salen complex. Applicants found that a preferred supported dimeric aluminium salen complex will have a size of about 10 to 2000 μm. For such a catalyst a 10 μm filter would be suitable. The filter may be for example so-called Johnson Screens® using Vee-Wire® filter elements.

In step (c) the halide compound is separated from the cyclic carbonate product. If carbon dioxide and/or epoxide compound are present in the mixture to be separated it is desired to also separate these compounds from the cyclic carbonate product. The carbon dioxide and/or epoxide compound may be recycled to step (a). Such a separation may be achieved by crystallisation, absorption, adsorption, extraction and/or distillation. Preferably the separation is performed in a distillation step. Distillation is advantageous because it can be performed in a continuous manner. In order to avoid that any epoxide compound converts to for example aldehydes and/or ketones at the relatively high reboiler temperatures of the distillation step it is preferred to reduce the content of epoxide compound in the mixture as obtained in step (b) before performing distillation step (c). In such a reduction step a mixture will be obtained having a reduced epoxide content. This mixture may then be separated in the distillation step (c).

The reduction of epoxide compound in the mixture obtained in step (b) may be achieved by extraction, stripping or chromatography. For example stripping with carbon dioxide would result in a mixture of carbon dioxide and epoxide compound which can be used in step (a) as reactants. Another method for reducing this content of epoxide compound may be achieved by contacting the epoxide compound with carbon dioxide in the presence of supported dimeric aluminium salen complex in a second reaction step. This reaction may be performed as described for step (a) above. Alternatively the supported dimeric aluminium salen compound may be immobilised in a fixed bed tubular reactor or a trickle bed reactor.

It has been found that this process may yield cyclic carbonate products having a very high purity. For example when preparing propylene carbonate purities of above 99 wt % and even above 99.999 wt % are achievable. The distillation may be performed in one or more distillation steps. Suitably carbon dioxide, halide compound, epoxide compound and the cyclic carbonate product are obtained as separate streams provided they are present in the feed to the distillation step. Typically the cyclic carbonate will have the highest boiling point and will be obtained as a bottom product of a distillation step. The distillation may be performed in one column wherein the different compounds are withdrawn from the column according to their boiling point.

Preferably all or part of the carbon dioxide as obtained in step (c) is directly or indirectly recycled to step (a). In this way all or almost all of the carbon dioxide can be converted to the cyclic carbonate. By indirectly recycled is here meant that the carbon dioxide is temporally stored before being recycled to step (a). A purge of the carbon dioxide as obtained in step (c) may be part of the process. This purge is advantageous because it avoids a build up of impurities in the feed and by-products, such as nitrogen, oxygen, water, acetic acid, methanol, aldehydes and ketones.

Preferably all or part of the epoxide as obtained in step (c) is directly or indirectly recycled to step (a). In this way all or almost all of the epoxide can be converted to the cyclic carbonate. By indirectly recycled is here meant that the epoxide is temporally stored before being recycled to step (a). A purge of the epoxide as obtained in step (c) may be part of the process. This purge is advantageous because it avoids a build-up of compounds boiling in the same range as the epoxide which may be present in any one of the feedstocks or which may have formed in the process.

Suitably all or part of the halide compound as obtained in step (c) is used to activate deactivated supported dimeric salen complex. This may be by directly recycling the halide compound to step (a) or by temporally storing the halide compound before using it to activate the catalyst. A purge of the halide compound as obtained in step (c) may be part of the process. This purge is advantageous because it avoids a build-up of compounds boiling in the same range as the halide compound which may be present in any one of the feedstocks or which may have formed in the process.

The reactivation of the supported dimeric aluminium salen complex may be performed by recycling the halide compound to step (a) as described above and/or by adding fresh halide compound. Preferably the reactivation of the supported dimeric aluminium salen complex is performed in a separate step (e). In such a step (e) the supported dimeric aluminium salen complex used in step (a) is contacted with the halide compound resulting in that the deactivated complexes reactivate. Preferably no carbon dioxide and/or epoxide is added to reactivation step (e). Some dissolved carbon dioxide and/or epoxide as added to the complex in step (a) may still be present. Preferably part of the cyclic carbonate product as present as reaction medium in step (a) is separated from the supported dimeric aluminium salen complex. This may be performed by means of the separation means used in step (b). This results in a suspension of liquid cyclic carbonate and the supported dimeric aluminium salen complex which is richer in the supported dimeric aluminium salen complex as compared to the suspension of step (a). Preferably the molar ratio of halide compound and the dimeric aluminium salen complex in this suspension in step (e) is greater than 5:1 and preferably greater than 7:1 in step (e).

When step (e) is performed it is preferred to store the halide compound obtained in step (c) and recycle the carbon dioxide and optionally the epoxide compound obtained in step (c). The stored halide compound may then be used in the separate step (e). Step (e) may be performed in different modes. For example a reactor in which step (a) is performed may regenerated in a step (e) wherein the supported dimeric aluminium salen complex remains in the reactor and halide compound is provided to the reactor. This results in that the reactor is temporarily not preparing cyclic carbonate because it is in its regeneration mode. In such a mode it is preferred to have at least more than one parallel operating reactors, wherein step (a) and (e) are alternatingly performed in a reactor and while step (e) is performed in one or more reactors step (a) is performed in the one or more remaining reactors.

In another mode the content or part of the content of the reactor in which step (a) is performed and comprising at least the supported dimeric aluminium salen complex is discharged from the reactor and provided to a different regeneration vessel in which step (e) is performed to obtain reactivated supported dimeric aluminium salen complex. The reactivated supported dimeric aluminium salen complex may be suitably returned to the reactor. By continuously replacing deactivated supported dimeric aluminium salen complex by reactivated supported dimeric aluminium salen complex it becomes possible to continuously perform step (a) in the reactor while the activity of the catalyst remains constant. Preferably all or part of the catalyst rich fraction obtained in step (b) is supplied to this regeneration vessel to perform step (e). For example if step (b) is performed by filtration a retentate rich in catalyst complex is obtained. Preferably all or part of this retentate is supplied to the regeneration vessel while the remaining part may be returned to the reactor. In case step (b) is performed by a hydrocyclone also a fraction rich in catalyst complex will be obtained which fraction may in total or partly be supplied to the regeneration vessel.

The epoxide may be the epoxides as described in the afore mentioned EP2257559B1 in paragraphs 22-26. Preferably the epoxide compound has 2 to 8 carbon atoms. Preferred epoxide compounds are ethylene oxide, propylene oxide, butylene oxide, pentene oxide, glycidol and styrene oxide. The cyclic carbonate products which may be prepared from these preferred epoxides have the general formula:

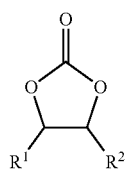

Where $R^1$ is a hydrogen or a group having 1-6 carbon atoms, preferably hydrogen, methyl, ethyl, propyl, hydroxymethyl and phenyl, and $R^2$ is hydrogen.

The supported dimeric aluminium salen complex may be any supported complex as disclosed by the earlier referred to EP2257559B1. Preferably the complex is represented by the following formula:

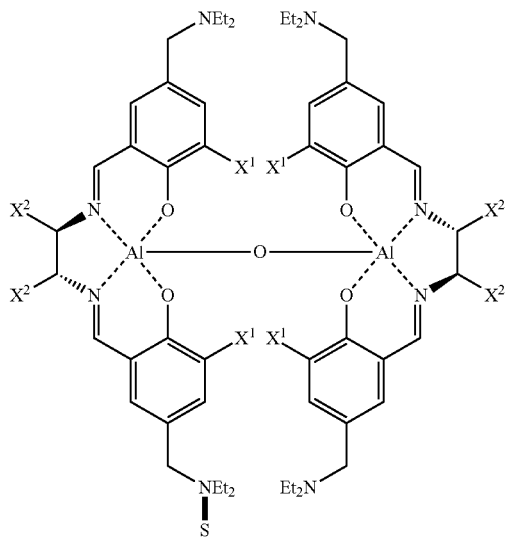

wherein S represents a solid support connected to the nitrogen atom via an alkylene bridging group, wherein the supported dimeric aluminium salen complex is activated by a halide compound. The alkylene bridging group may have between 1 and 5 carbon atoms. X2 may be a C6 cyclic alkylene or benzylene. Preferably X2 is hydrogen. X1 is preferably a tertiary butyl. Et in the above formula represents any alkyl group, preferably having from 1 to 10 carbon atoms. Preferably Et is an ethyl group.

S represents a solid support. The catalyst complex may be connected to such a solid support by (a) covalent binding, (b) steric trapping or (c) electrostatic binding. For covalent binding, the solid support S needs to contain or be derivatized to contain is reactive functionalities which can serve for covalently linking a compound to the surface thereof. Such materials are well known in the art and include, by way of example, silicon dioxide supports containing reactive Si—OH groups, polyacrylamide supports, polystyrene supports, polyethyleneglycol supports, and the like. A further example is sol-gel materials. Silica can be modified to include a 3-chloropropyloxy group by treatment with (3-chloropropyl)triethoxysilane. Another example is Al pillared clay, which can also be modified to include a 3-chloropropyloxy group by treatment with (3-chloropropyl)triethoxysilane. Solid supports for covalent binding of particular interest in the present invention include siliceous MCM-41 and MCM-48, optionally modified with 3-aminopropyl groups, ITQ-2 and amorphous silica, SBA-15 and hexagonal mesoporous silica. Also of particular interest are sol-gels. Other conventional forms may also be used. For steric trapping, the most suitable class of solid support is zeolites, which may be natural or modified. The pore size must be sufficiently small to trap the catalyst but sufficiently large to allow the passage of reactants and products to and from the catalyst. Suitable zeolites include zeolites X, Y and EMT as well as those which have been partially degraded to provide mesopores, that allow easier transport of reactants and products. For the electrostatic binding of the catalyst to a solid support, typical solid supports may include silica, Indian clay, Al-pillared clay, Al-MCM-41, K10, laponite, bentonite, and zinc-aluminum layered double hydroxide. Of these silica and montmorillonite clay are of particular interest. Preferably the support S is a particle chosen from the group consisting of silica, alumina, titania, siliceous MCM-41 or siliceous MCM-48.

Preferably the support S has the shape of a powder having dimensions which are small enough to create a high active catalytic surface per weight of the support and large enough to be easily separated from the cyclic carbonate in step (b). Preferably the support powder particles have for at least 90 wt % of the total particles a particle size of above 10 μm and below 2000 μm. The particle size is measured by a Malvern® Mastersizer® 2000.

The supported catalyst complex as shown above is activated by a halide compound. The halide may be Cl, Br or I and preferably Br. The quaternary nitrogen atom of the complex shown above is paired with the halide counterion. The halide compound preferably has the form R4NY, where each R is independently C1-10 alkyl or a C6-C8 aryl and Y is selected from I, Br and Cl. R is may be a C3-5alkyl, and more preferably butyl. Preferably R is a benzyl group. Y is preferably Br. Therefore, a particularly preferred co-catalysts are benzyl bromide and Bu4NBr (TBAB). Benzyl bromide is advantageous because it can be separated from propylene oxide and propylene carbonate by distillation in a process to prepare propylene carbonate. Benzyl bromide is advantageous because it can be separated from ethylene oxide and ethylene carbonate by distillation in a process to prepare ethylene carbonate.

An example of a preferred supported dimeric aluminium salen complex which complex is activated by benzyl bromide is shown below, wherein Et is ethyl and tBu is tert-butyl and Osilica represents a silica support:

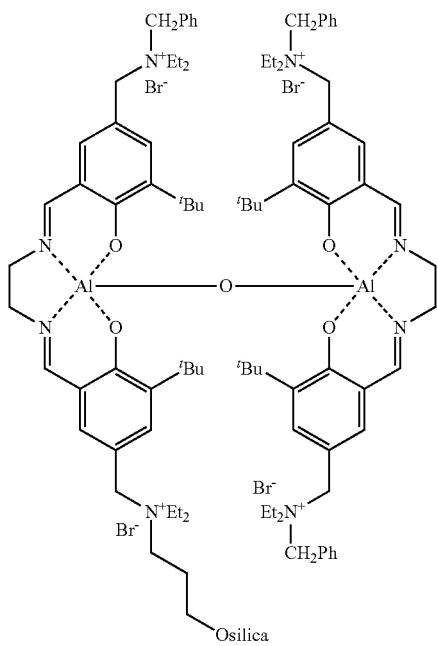

In use the Et group in the above formula may be exchanged with the organic group of the halide compound. For example if benzyl bromide is used as the halide compound to activate the above supported dimeric aluminium salen complex the Et group will be exchanged with the benzyl group when the catalyst is reactivated.

Figure 2:
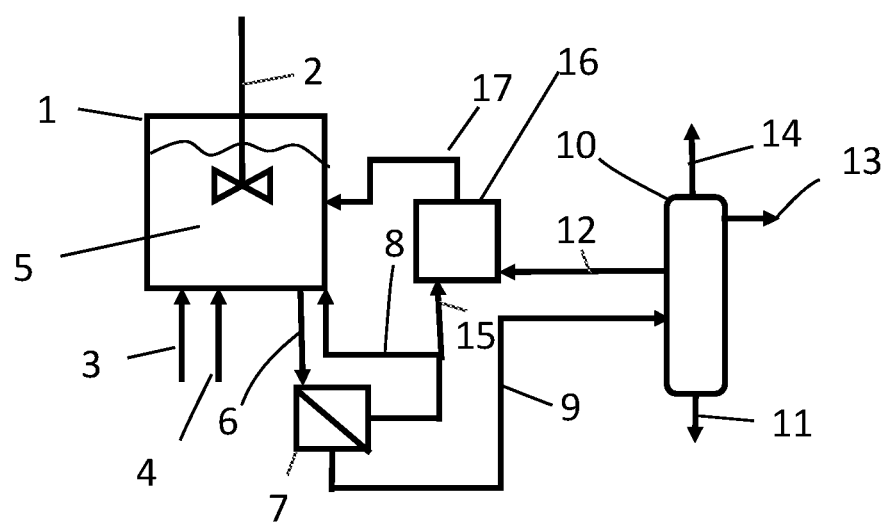

The invention will be illustrated by FIGS. 1-2 which illustrate a process to prepare propylene carbonate from carbon dioxide and propylene oxide. FIG. 1 shows 1 a continuously operated stirred reactor 1 provided with stirring means 2. To reactor 1 carbon dioxide in stream 3 and propylene oxide in stream 4 are continuously supplied. The reactor 1 further contains a suspension of liquid cyclic carbonate and the supported dimeric aluminium salen complex which complex is activated by a halide compound. From the reactor 1 a suspension of liquid cyclic carbonate, the supported dimeric aluminium salen complex which complex is activated by benzyl bromide, carbon dioxide and propylene oxide is continuously withdrawn as stream 6 and fed to a cross-flow filtration unit 7. In unit 7 a stream 8 is obtained which is a suspension of liquid propylene carbonate and enriched in supported dimeric aluminium salen complex which complex is activated by benzyl bromide and poor in carbon dioxide, propylene oxide and benzyl bromide. The unit 7 further yields a stream 9 which is a mixture of the propylene carbonate product, carbon dioxide, propylene oxide and halide compound as separated from the reaction mixture of stream 6. This stream 9 is fed to a distillation column 10. In distillation column 10 a purified propylene carbonate product is obtained as bottom stream 11, benzyl bromide as stream 12, propylene oxide and water as stream 13 and carbon dioxide as stream 14. Streams 13 and 14 may be fed to reactor 1. A purge may be provided for both streams 13 and 14 to avoid a build-up of non-reacting compounds. The stream 12 of benzyl bromide may be fed to a storage to be used in a regeneration step (e) of reactor 1. A purge may be provided for stream 12 to avoid a build-up of non-reacting compounds.

FIG. 2 shows a process flow scheme wherein stream 12 is continuously used to regenerate the catalyst complex of reactor 1. FIG. 2 shows the same reactors and unit operations as in FIG. 1. In addition a stream 15 is shown which directs part of stream 8 to a regeneration vessel 16. Also stream 12 is fed to vessel 16. In this way the catalyst complex can be regenerated with the halide compound of stream 12. The reactivated catalyst is fed to reactor 1 in stream 17.

Figure 3:
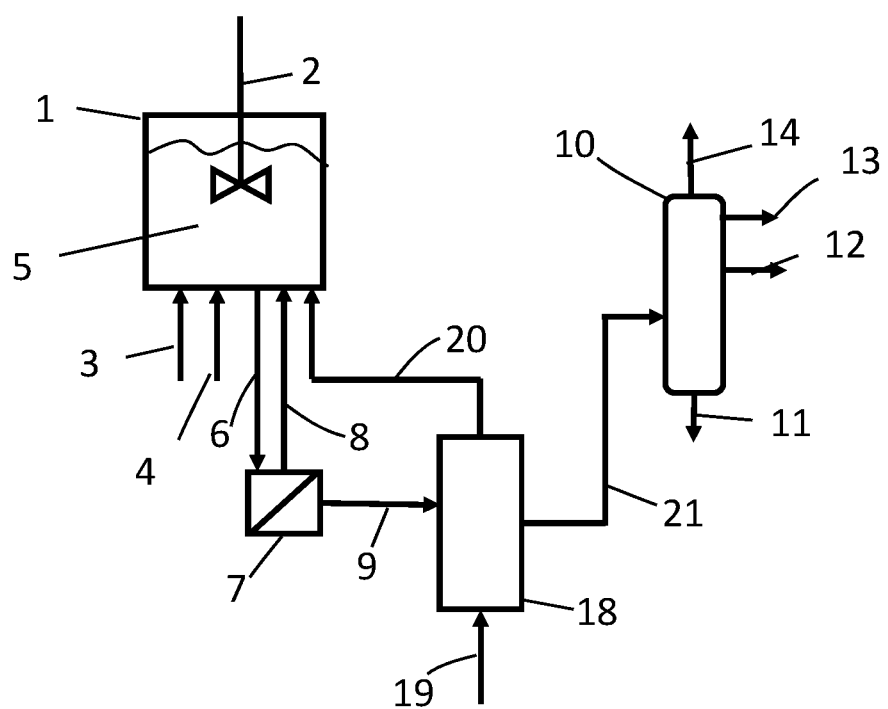

FIG. 3 shows a scheme like in FIG. 1 except in that the filtered reaction mixture of stream 9 is now fed to a stripper-reactor 18. To this stripper-reactor 18 a flow of carbon dioxide 19 counter-currently contacts the reaction mixture. Part of the propylene oxide present in stream 9 will be stripped out of the mixture and returned to reactor 1 via stream 20. At the lower end of stripper-reactor 18 a mixture poor in propylene oxide is obtained as stream 21 and provided to a distillation column 10. The remaining streams are as in FIG. 1.

The invention claimed is:

1. A process to continuously prepare a cyclic carbonate product by reacting an epoxide compound with carbon dioxide in the presence of a supported dimeric aluminium salen complex which complex is activated by a halide compound comprising the following steps,
(a) contacting carbon dioxide with the epoxide compound in a suspension of liquid cyclic carbonate and the supported dimeric aluminium salen complex which complex is activated by a halide compound, wherein the epoxide compound reacts with the carbon dioxide to the cyclic carbonate product and part of the supported dimeric salen complex deactivates,
(b) separating part of the cyclic carbonate product from the supported dimeric aluminium salen complex, to obtain a mixture comprising of the cyclic carbonate product, carbon dioxide, epoxide compound and halide compound, (c) separating the halide compound from the cyclic carbonate product to obtain purified cyclic carbonate product by distillation and wherein in the distillation a mixture comprising of carbon dioxide, halide compound, the epoxide compound and the cyclic carbonate product is separated into separate streams of carbon dioxide, halide compound, epoxide compound and the cyclic carbonate product, and wherein the deactivated supported dimeric aluminium salen complex is reactivated, either as part of the continuous process or as a separate batch or semi-batch operation, by contacting the deactivated supported dimeric aluminium salen complex with the halide compound in the presence of the cyclic carbonate product.

2. The process according to claim 1, wherein the temperature in step (a) is between 20 and 150° C. and the pressure is between 0.1 and 0.5 MPa and wherein temperature is below the boiling temperature of the product at the chosen pressure.

3. The process according to claim 1, wherein step (a) is performed in a continuously operated stirred reactor wherein carbon dioxide and epoxide compound are continuously supplied to the reactor and wherein part of the cyclic carbonate product is continuously withdrawn as part of a liquid stream.

4. The process according to claim 1, wherein the epoxide compound has 2 to 8 carbon atoms.

5. The process according to claim 4, wherein the epoxide compound is ethylene oxide, propylene oxide, butylene oxide, pentene oxide, glycidol or styrene oxide.

6. The process according to claim 1, wherein the separation in step (b) makes use of the different mass density and/or size between the cyclic carbonate and the supported dimeric aluminium salen complex.

7. The process according to claim 6, wherein the separation of step (b) is performed by means of a filter.

8. The process according to claim 6, wherein the separation of step (b) is performed using centrifugal forces.

9. The process according to claim 1, wherein the content of epoxide compound in the mixture as obtained in step (b) is reduced to obtain a mixture having a reduced epoxide content which obtained mixture is separated in the distillation step (c).

10. The process according to claim 9, wherein the reduction of the epoxide compound is achieved by contacting the epoxide compound with carbon dioxide in the presence of supported dimeric aluminium salen complex in a second reaction step.

11. The process according to claim 1, wherein the molar ratio of halide compound and the supported dimeric aluminium salen complex is greater than 5:1 in step (e).

12. The process according to claim 1, wherein step (a) and (e) is performed in two or more parallel operated reactors and when step (e) is performed in one or more reactors and step (a) is performed in at least one of the remaining reactors.

13. The process according to claim 1, wherein the supported dimeric aluminium salen complex is represented by the following formula:

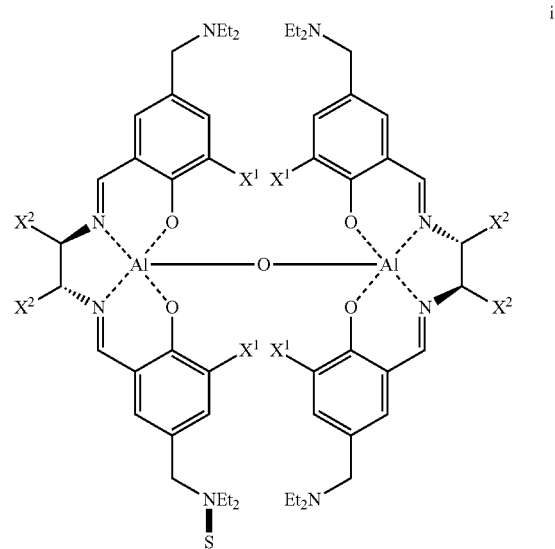

wherein S represents a solid support connected to the nitrogen atom via an alkylene group, wherein the supported dimeric aluminium salen complex is activated by a halide compound and wherein $X^1$ is tertiary butyl and $X^2$ is hydrogen and wherein Et is an alkyl group having 1 to 10 carbon atoms.

14. The process according to claim 13, wherein the support S is composed of particles having an average diameter of between 10 and 2000 μm.

15. The process according to claim 14, wherein the support S is a particle chosen from the group consisting of silica, alumina, titania, siliceous MCM-41 or siliceous MCM-48.

16. The process according to claim 1, wherein the halide compound is benzyl halide.

17. The process according to claim 16, wherein the benzyl halide is benzyl bromide.

* * * * *